US011676281B2

(12) United States Patent
Nikolov et al.

(10) Patent No.: US 11,676,281 B2
(45) Date of Patent: *Jun. 13, 2023

(54) 3-D CONVOLUTIONAL NEURAL NETWORKS FOR ORGAN SEGMENTATION IN MEDICAL IMAGES FOR RADIOTHERAPY PLANNING

(71) Applicant: Google LLC, Mountain View, CA (US)

(72) Inventors: Stanislav Nikolov, London (GB); Samuel Blackwell, London (GB); Jeffrey De Fauw, London (GB); Bernardino Romera-Paredes, London (GB); Clemens Ludwig Meyer, London (GB); Harry Askham, London (GB); Cian Hughes, London (GB); Trevor Back, Saffron Walden (GB); Joseph R. Ledsam, Tokyo (JP); Olaf Ronneberger, London (GB)

(73) Assignee: Google LLC, Mountain View, CA (US)

( * ) Notice: Subject to any disclaimer, the term of this patent is extended or adjusted under 35 U.S.C. 154(b) by 66 days.

This patent is subject to a terminal disclaimer.

(21) Appl. No.: 17/380,914

(22) Filed: Jul. 20, 2021

(65) Prior Publication Data

US 2022/0012891 A1    Jan. 13, 2022

Related U.S. Application Data

(63) Continuation of application No. 16/565,384, filed on Sep. 9, 2019, now Pat. No. 11,100,647.

(Continued)

(51) Int. Cl.
*G06T 7/11* (2017.01)
*G06T 7/62* (2017.01)
(Continued)

(52) U.S. Cl.
CPC .............. *G06T 7/11* (2017.01); *A61B 5/7267* (2013.01); *A61B 6/032* (2013.01); *A61B 6/501* (2013.01);
(Continued)

(58) Field of Classification Search
CPC ...................... G06T 2207/20084; G06T 7/11
See application file for complete search history.

(56) References Cited

U.S. PATENT DOCUMENTS 10,198,832 B2 * 2/2019 De Fauw ............. G06V 10/764
10,878,270 B1 * 12/2020 Cao ........................ G06V 10/82
(Continued)

FOREIGN PATENT DOCUMENTS

EP          3355270         8/2018

OTHER PUBLICATIONS

Bans. Kayallbay, CNN-based Segmentation of Medical Imaging Data, Computer Vision and Pattern Recognition, Jul. 2017, p. 1-24.
(Continued)

*Primary Examiner* — Gandhi Thirugnanam
(74) *Attorney, Agent, or Firm* — Fish & Richardson P.C.

(57) ABSTRACT

Methods, systems, and apparatus, including computer programs encoded on a computer storage medium, for segmenting a medical image. In one aspect, a method comprises: receiving a medical image that is captured using a medical imaging modality and that depicts a region of tissue in a body; and processing the medical image using a segmentation neural network to generate a segmentation output. The segmentation neural network can include a sequence of multiple encoder blocks and a decoder subnetwork. Training the segmentation neural network can include determining a set of error values for a segmentation channel; identifying the highest error values from the set of error values for the segmentation channel; and determining a segmentation loss
(Continued)

based on the highest error values identified for the segmentation channel.

20 Claims, 8 Drawing Sheets

Related U.S. Application Data

(60) Provisional application No. 62/729,054, filed on Sep. 10, 2018.

(51) Int. Cl.
    *A61B 5/00*       (2006.01)
    *A61B 6/03*       (2006.01)
    *A61B 6/00*       (2006.01)
    *A61N 5/10*       (2006.01)
    *G06N 3/08*       (2023.01)

(52) U.S. Cl.
    CPC .............. *A61N 5/1039* (2013.01); *G06N 3/08* (2013.01); *G06T 7/62* (2017.01); *G06T 2207/10081* (2013.01); *G06T 2207/20081* (2013.01); *G06T 2207/20084* (2013.01); *G06T 2207/30196* (2013.01)

(56) References Cited

U.S. PATENT DOCUMENTS

| | | | |
|---|---|---|---|
| 11,100,647 B2* | 8/2021 | Nikolov | G06N 3/08 |
| 2005/0163375 A1* | 7/2005 | Grady | G06T 7/162 |
| | | | 382/180 |
| 2013/0230247 A1* | 9/2013 | Schlosser | G06K 9/6267 |
| | | | 382/180 |
| 2013/0279801 A1* | 10/2013 | Scheuermann | G06T 7/187 |
| | | | 382/164 |
| 2015/0206022 A1* | 7/2015 | Radha Krishna Rao | |
| | | | G06V 10/764 |
| | | | 382/128 |
| 2017/0109881 A1* | 4/2017 | Avendi | G06T 7/38 |
| 2018/0033144 A1* | 2/2018 | Risman | G06T 9/002 |
| 2019/0005360 A1* | 1/2019 | Heide | G06N 3/0454 |
| 2019/0005684 A1* | 1/2019 | De Fauw | G06V 10/764 |
| 2019/0030371 A1* | 1/2019 | Han | G06T 7/11 |
| 2019/0139216 A1* | 5/2019 | Georgescu | G16H 30/40 |
| 2019/0139270 A1* | 5/2019 | De Fauw | G06K 9/6292 |
| 2019/0205758 A1* | 7/2019 | Zhu | G06K 9/6256 |
| 2019/0244086 A1* | 8/2019 | Franca-Neto | G06N 3/0454 |
| 2020/0082534 A1* | 3/2020 | Nikolov | G06T 7/0012 |
| 2021/0019889 A1* | 1/2021 | Novikov | G06N 3/08 |
| 2021/0027098 A1 | 1/2021 | Ge | |

OTHER PUBLICATIONS

Bosch et al., "Head-neck cetuximab—the cancer imaging archive," 2015, 2 pages.
Brouwer et al., "CT-based delineation of organs at risk in the head and neck region: DAHANCA, EORTC, GORTEC, HKNPCSG, NCIC CTG, NCRI, NRG oncology and TROG consensus guidelines," Radiother. Oncol., vol. 117, No. 1, pp. 83-90, Oct. 2015, 8 pages.
Cancer Research UK, "Head and neck cancers incidence statistics," https://www.cancerresearchuk.org/health-professional/cancer-statistics/statistics-by-cancer-type/head-and-neck-cancers/incidence#heading-Two, Feb. 2018, accessed: Feb. 8, 2018, 19 pages.
Caudell et al., "Dosimetric factors associated with long-term dysphagia after definitive radiotherapy for squamous cell carcinoma of the head and neck," Int. J. Radiat. Oncol. Biol. Phys., vol. 76, No. 2, pp. 403-409, Feb. 2010, 7 pages.
Chen et al., "The relationship between waiting time for radiotherapy and clinical outcomes: a systematic review of the literature," Radiother. Oncol., vol. 87, No. 1, pp. 3-16, Apr. 2008, 14 pages.
Chu et al., "Applying machine learning to automated segmentation of head and neck tumour volumes and organs at risk on radiotherapy planning ct and mri scans," F1000 Research, vol. 5, No. 2104, 2016.
Çiçek et al., "3D U-Net: learning dense volumetric segmentation from sparse annotation," in Med Image Comput Comput Assist Interv, pp. 424-432, 2016, 9 pages.
Clark et al., "The cancer imaging archive (TCIA): maintaining and operating a public information repository," J Digit Imaging, vol. 26, No. 6, pp. 1045-1057, Dec. 2013, 13 pages.
Cui et al, "Deep Convolutional Encoder-Decoder Architecture for Neuronal Structure Segmentation," IEEE, May 19, 2018, 6 pages.
Daisne et al., "Atlas-based automatic segmentation of head and neck organs at risk and nodal target volumes: a clinical validation," Radiat. Oncol., vol. 8, p. 154, Jun. 2013, 11 pages.
De Fauw et al., "Clinically applicable deep learning for diagnosis and referral in retinal disease," Nat. Med., vol. 24, pp. 1342-1350, Aug. 2018, 15 pages.
Dice, "Measures of the amount of ecologic association between species," Ecology, vol. 26, No. 3, pp. 297-302, Jul. 1945, 7 pages.
Dirix et al., "Dysphagia after chemoradiotherapy for head-and-neck squamous cell carcinoma: Dose-effect relationships for the swallowing structures," Int J Radiat Oncol Biol Phys, vol. 75, No. 2, pp. 385-392, Oct. 2009, 8 pages.
Duc et al., "Validation of clinical acceptability of an atlas-based segmentation algorithm for the delineation of organs at risk in head and neck cancer," Med. Phys., vol. 42, No. 9, pp. 5027-5034, 2015, 9 pages.
Felzenszwab et al., "Distance transforms of sampled functions," Theory Comput., vol. 8, No. 19, pp. 415-428, 2012, 14 pages.
Fortunati et al., "Tissue segmentation of head and neck CT images for treatment planning: a multiatlas approach combined with intensity modeling," Med. Phys., vol. 40, No. 7, p. 071905, Jul. 2013, 15 pages.
Fritscher et al., "Deep neural networks for fast segmentation of 3D medical images," in Med Image Comput Comput Assist Interv. Springer International Publishing, pp. 158-165, 2016, 8 pages.
Harari et al., "Emphasizing conformal avoidance versus target definition for IMRT planning in head-and-neck cancer," Int. J. Radiat. Oncol. Biol. Phys., vol. 77, No. 3, pp. 950-958, Jul. 2010, 9 pages.
He et al., "Deep residual learning for image recognition," arXiv, Dec. 2015, 12 pages.
Hoogeman et al., "Atlas-based auto-segmentation of CT images in head and neck cancer: What is the best approached?" Int. J. Radiat. Oncol. Iol. Phys., vol. 72, No. 1, p. S591, Sep. 2008, 1 page.
https://stackoverflow.com/questions/41409248/softmax-and-sigmoid-function-for-the-output-layer/41409315, "softmax and sigmoid function for the output layer", Author Unknown, Dec. 2016 (Year: 2016).
Ibragimov et al., "Segmentation of organs-at-risks in head and neck CT images using convolutional neural networks," Med. Phys., vol. 44, No. 2, pp. 547-557, 2017, 13 pages.
Jemal et al., "Global cancer stastics," CA Cancer J. Clin., vol. 61, No. 2, 69-90, Mar. 2011, 22 pages.
Jensen et al., "Late swallowing dysfunction and dysphagia after radiotherapy for pharynx cancer: frequency, intensity and correlation with does and volume parameters," Radiother. Oncol., vol. 85, No. 1, pp. 74-82, Oct. 2009, 16 pages.
Kayalibay et al, "CNN-Based Segmentation of the Medical Imaging Data," arXiv, Jan. 11, 2017, 24 pages.
Kingma et al., "Adam: a method for stochastic optimization," arXiv, Dec. 2014, 15 pages.
Levendag et al., "Atlas based auto-segmentation of CT images: clinical evaluation of using auto-contouring in high-dose, high-precision radiotherapy of cancer in the heand and neck," Int. J. Radiat. Oncol. Biol. Phys., vol. 72, No. 1, p. S401, Sep. 2008.
Mikeljevic et al., "Trends in postoperative radiotherapy delay and the effect on survival in breast cancer patients treated with conservation surgery," Br. J. Cancer, vol. 90, No. 7, pp. 1343-1348, Apr. 2004, 6 pages.
Mocnik et al., "Segmentation of parotid glands from registered CT and MR images," Phys. Med., vol. 52, pp. 33-41, Aug. 2018, 9 pages.

(56) References Cited

OTHER PUBLICATIONS

National Cancer Intelligence Network, "NCIN data briefing: Potentially HPV-related head and neck cancers," http://www.ncin.org.uk/publications/data_briefings/potentially_hpv_related_head_and_neck_cancers, May 2012.

Nelms et al., "Variations in the contouring of organs at risk: test case from a patient with oropharyngeal cancer," Int. J. Radiat. Oncol. Biol. Phys., vol. 82, No. 1, pp. 368-378, Jan. 2012, 11 pages.

Nikolov et al., "Deep learning to achieve clinically applicable segmentation of head and neck anatomy for radiotherapy" arXiv:1809.04430, Sep. 12, 2018, 31 pages.

Nutting et al., "Parotid-sparing intensity modulated versus conventional radiotherapy in head and neck cancer (PARSPORT): a pahse 3 multicentre randomised controlled trial," Lancet Oncol., vol. 12, No. 2, pp. 127-136, Feb. 2011, 10 pages.

Oxford Cancer Intelligence Unit, "Profile of head and neck cancers in england: Incidence, mortality and survival," National Cancer Intelligence Network, Tech. Rep., 2010.

Parkin et al., "16. the fraction of cancer attributable to lifestyle and enviromental factors in the UK in 2010," Br. J. Cancer, vol. 105, No. S2, pp. S77-S81, Dec. 6, 2011, 5 pages.

PCT International Search Report and Written Opinion in International Appln. No. PCT/EP2019/074119, dated Oct. 23, 2019, 17 pages.

Qazi et al., "Auto-segmentation of normal and target structures in head and neck CT images: A feature-driven model-based approach," Med. Phys., vol. 38, No. 11, pp. 6160-6170, 2011, 12 pages.

Raudaschl et al., "Evaluation of segmentation methods on head and neck CT: Auto-segmentation challenge 2015," Med. Phys., vol. 44, No. 5, pp. 2020-2036, 2017, 40 pages.

Ren et al., "Interleaved 3D-CNNs for joint segmentation of small-volume structures in head and neck CT images," Med. Phys., vol. 45, No. 5, pp. 2063-2075, May 2018, 42 pages.

Ronneberger et al., U-Net: convolutional networks for biomedical image segmentation,: in Med. Image Comput Comput Assist Interv., Springer International Publishing, pp. 234-241, 2015, 8 pages.

Rosenblatt, "Radiotherapy in cancer care: Facing the global challenge," International Atomic Energy Agency, Tech. Rep., 2017, 578 pages.

Round et al., "Radiotherapy demand and activity in england 2006-2020," Clin. Oncol., vol. 25, No. 9, pp. 522-530, Sep. 2013, 9 pages.

Sharp et al., "Vision 20/20: perspectives on automated image segmentation for radiotherapy," Med. Phys., vol. 41, No. 5, p. 050902, May 2014.

Sims et al., "A pre-clinical assessment of an atlas-based automatic segmentation tool for the head and neck," Radiother. Oncol., vol. 93, No. 3, pp. 474-478, Dec. 2009, 5 pages.

Tam et al., "Automated delineation of organs-at-risk in head and neck CT images using multi-output support vector regression," in Medical Imaging 2018: Biomedical Applications in Molecular, Structural, and Functional Imaging, vol. 10578. International Society for Optics and Photonics, p. 1057824, Mar. 2018, 3 pages.

Teguh et al., "Clinical validation of atlas-based auto-segmentation of multiple target volumes and normal tissue (swallowing/mastication) structures in the head and neck," Int. J. Radiat. Oncol. Biol. Phys., vol. 81, No. 4, pp. 950-957, Nov. 2011, 8 pages.

Thomson et al., "Evaluation of an automatic segmentation algorithm for definition of head and neck organs at risk," Radiat. Oncol., vol. 9, p. 173, Aug. 2014, 12 pages.

Tong et al, "Fully automatic multi-organ segmentation for head and neck cancer radiotherapy using shape representation model constrained fully convultional neural networks," Medical Physics, Oct. 1, 2018, 10 pages.

Tong et al., "Fully automatic multi-organ segmentation for head and neck cancer radiotherapy using shape representation model constrained fully convolutional neural networks," Medical Physics, vol. 0, No. ja, 2018.

Veiga et al., "Toward adaptive radiotherapy for head and neck patients: Feasibility study on using ct-to-cbcy deformable registration for 'dose of the day' calculations," Med. Phys., vol. 41, No. 3, p. 031703 (12 pp.), 2014, 13 pages.

Voet et al., "Does atlas-based autosegmentation of neck levels require subsequent manual contour editing to avoid risk of severe target underdosage? A dosimetric analysis," Radiother. Oncol., vol. 98, No. 3, pp. 373-377, Mar. 2011, 5 pages.

Walker et al., "Prospective randomized double-blind study of atlas-based organ-at-risk autosegmentation-assisted radiation planning in head and neck cancer," Radiother. Oncol., vol. 112, No. 3, pp. 321-325, Sep. 2014, 5 pages.

Wang et al., "Hierarchical vertex regression-based segmentation of head and neck CT images for radiotherapy planning," IEEE Trans. Image Process., vol. 27, No. 2, pp. 923-937, Feb. 2018, 15 pages.

Wu et al., "Bridging category-level and instance-level semantic image segmentation," arXiv, May 2016, 14 pages.

Wuthrick et al., "Institutional clinical trial accrual volume and survival of patients with head and neck cancer," Journal of Clinical Oncology, vol. 33, No. 2, pp. 156-164, 2015, pMID: 25488965, 13 pages.

Zhu et al., "AnatomyNet: Deep 3D squeeze-and-excitation U-Nets for fast and fully automated whole-volume anatomical segmentation," arXiv, Aug. 2018, 13 pages.

Zuley et al., "Radiology data from the cancer genome atlas head-neck squamous cell carcinoma [TCGA-HNSC] collection," 2016, 2 pages.

* cited by examiner

3-D CONVOLUTIONAL NEURAL NETWORKS FOR ORGAN SEGMENTATION IN MEDICAL IMAGES FOR RADIOTHERAPY PLANNING

CROSS-REFERENCE TO RELATED APPLICATION

This patent application is a continuation (and claims the benefit of priority under 35 USC 120) of U.S. patent application Ser. No. 16/565,384, filed Sep. 9, 2019, which claims priority under 35 U.S.C. 119 to Provisional Application No. 62/729,054, filed Sep. 10, 2018, which is incorporated by reference.

BACKGROUND

This specification relates to processing medical images using machine learning models.

Medical images can be captured using a variety of imaging modalities, e.g., a computerized tomography (CT) imaging modality.

Machine learning models receive an input and generate an output, e.g., a predicted output, based on the received input. Some machine learning models are parametric models and generate the output based on the received input and on values of the parameters of the model.

Some machine learning models are deep models that employ multiple layers of models to generate an output for a received input. For example, a deep neural network is a deep machine learning model that includes an output layer and one or more hidden layers that each apply a non-linear transformation to a received input to generate an output.

SUMMARY

This specification describes a system and methods implemented as computer programs on one or more computers in one or more locations that perform medical image segmentation. The segmentations generated by the system can be provided for presentation to a user, e.g., to assist a physician or other medical professional.

According to a first aspect there is provided a method comprising receiving a medical image that is captured using a medical imaging modality, and that depicts or represents a (3D) region of tissue in a body. The method comprises processing the medical image using a segmentation neural network to generate a segmentation output.

The segmentation output may comprise a plurality of segmentation channels, each segmentation channel corresponds to a respective organ from a predetermined set of organs, and each segmentation channel defines a segmentation of the respective organ corresponding to the segmentation channel in the medical image. A segmentation of a respective organ in the medical image may comprise, for each of a plurality of voxels in the medical image, a respective score characterizing whether the voxel corresponds to an interior of the respective organ (e.g. whether or not the tissue belongs to the organ). The score may comprise, or be processed to provide, a binary score to define a segmentation mask.

In some implementations the segmentation neural network comprises a sequence of encoder blocks. Each encoder block may be a residual neural network block comprising one or more two-dimensional convolutional neural network layers, one or more three-dimensional convolutional neural network layers, or both. Such a residual neural network block may have a connection which skips one or more non-linear layers of the block, e.g. a (direct) connection between an input and an output of the block. Each encoder block may be configured to process a respective encoder block input to generate a respective encoder block output. A (spatial) resolution of the encoder block output may be lower than a (spatial) resolution of the encoder block input. For each encoder block that is after an initial encoder block in the sequence of encoder blocks, the encoder block input may comprise a previous encoder block output of a previous encoder block in the sequence of encoder blocks. The segmentation neural network may also comprise a decoder subnetwork, configured to process a decoder subnetwork input comprising an intermediate output of each encoder block to generate the segmentation output.

In some implementations the segmentation neural network comprises a final layer which is configured to process a final layer input to generate the segmentation output. Processing the final layer input to generate the segmentation output may comprise processing the final layer input in accordance with a set of final layer weights to generate a transformed final layer input, and processing the transformed final layer input using a sigmoid activation function to generate the segmentation output.

Particular embodiments of the subject matter described in this specification can be implemented so as to realize one or more of the following advantages.

The segmentation neural network described in this specification achieves a performance level comparable to human experts (e.g., radiographers) in medical image segmentation. Therefore, the segmentation neural network has the potential to be deployed to a clinical setting where it could reduce healthcare costs and improve efficiency. For example, the segmentation neural network can be used as part of an automated radiotherapy treatment planning process to segment "organs at risk", that is, normal anatomical structures that are at risk of accidental irradiation during radiotherapy. In this example, the segmentation neural network can partially- or fully-automate a time-consuming task previously performed by experts.

The segmentation neural network can generate a segmentation as the output of a final neural network layer with an activation function (e.g., a sigmoid activation function) that is applied separately to each component of the segmentation output. By applying the activation function separately to each component of the segmentation output, the segmentation neural network can characterize a single voxel of a medical image as having a high probability of belonging to multiple organs. For example, the segmentation neural network can generate a segmentation output which characterizes a single voxel as having a high probability of belonging to both a "lens" and an "eye". In contrast, some conventional segmentation neural networks generate segmentation outputs which are unable to characterize a single voxel as belonging to multiple overlapping organs with high probability. For example, some conventional neural networks use a soft-max activation function in the final layer, where the soft-max function is jointly applied to groups of components of the segmentation output (i.e., where the components of a group characterize the likelihood that a voxel of the medical image belongs to different organs). In this example, the soft-max outputs for the components of each group are required to sum to 1, resulting in the conventional neural network being unable to characterize a single voxel as belonging to multiple organs with high probability. Therefore, unlike some conventional segmentation neural networks, the segmentation neural network described in this specification can be used to generate accurate segmentation outputs for multiple overlapping organs.

The medical imaging modality, or system, may comprise a computerized tomography (CT) medical imaging modality (or system), and/or another imaging modality such as MRI (magnetic resonance imaging) or a PET (Positron Emission Tomography) scan.

In some implementations the decoder subnetwork comprises a sequence of multiple decoder blocks. Each decoder block may comprise a residual neural network block comprising one or more two-dimensional convolutional neural network layers. Each decoder block may be configured to process a respective decoder block input to generate a respective decoder block output. A (spatial) resolution of the decoder block output is greater than a (spatial) resolution of the decoder block input. For each decoder block that is after an initial decoder block in the sequence of decoder blocks, the decoder block input may comprise: (i) an intermediate output of a respective encoder block, and (ii) a previous decoder block output of a previous decoder block. The three-dimensional convolutional neural network layers in the encoder blocks may comprise padded xy-convolutions and unpadded z-convolutions.

The segmentation neural network may include a linking block e.g. a residual neural network block comprising a fully-connected layer. The linking block may be configured to process a linking block input comprising an output of a final encoder block in the sequence of encoder blocks to generate a linking block output, which may be provided as an input to the decoder subnetwork.

The segmentation system described in this specification can characterize the accuracy of a predicted organ segmentation by computing a measure of agreement between the surfaces (i.e., rather than the whole volumes) of: (i) the predicted organ segmentation, and (ii) a ground truth organ segmentation. The measure of agreement between the surfaces may characterize the fraction of the surface of the predicted segmentation that would need to be manually corrected by an expert, e.g., to enable the segmentation to be used in radiotherapy planning. The segmentation system can train the segmentation neural network until its performance, measured based on segmentation surface agreement, achieves an acceptable level. Thereafter, the trained segmentation neural network may be incorporated into a clinical workflow, where experts may be required to spend minimal amounts of time on correcting the predicted segmentations generated by the segmentation neural network.

Thus in some implementations the method further comprises computing a surface measure e.g. a surface Dice measure or surface Dice-Sorensen coefficient, as a segmentation performance metric. The surface Dice measure may be computed between (i) a segmentation of a respective organ in the medical image defined by a segmentation channel from the segmentation output, and (ii) a reference e.g. human expert segmentation of the respective organ in the medical image. Computing the surface Dice measure may comprise determining a number of voxels in a first intersection between: (i) a surface of the segmentation of the respective organ, and (ii) a tolerance region around a surface of the reference segmentation of the respective organ; or determining a number of voxels in a second intersection between: (i) a surface of the reference segmentation of the respective organ, and (ii) a tolerance region around a surface of the segmentation of the respective organ; or both. Determining both has an advantage of penalizing both false positive and false negative parts of the predicted segmentation. Defining a tolerance region is clinically beneficial as it is an absolute deviation from a segmentation, e.g. in mm, which is important for radiotherapy treatment safety.

In implementations computing the surface Dice measure may further comprise determining the surface dice measure as a ratio of: (i) a sum of the number of voxels in the first intersection and the number of voxels in the second intersection, and (ii) a sum of a number of voxels in the surface of the segmentation of the respective organ and a number of voxels in the surface of the reference segmentation of the respective organ.

In principle such a surface measure may be computed independently of the segmentation technique used. Applications are not limited to the above described methods and the surface measure may be applied e.g. to any segmentation of an organ in a medical image which defines, for each of a plurality of voxels in the medical image, a value characterizing whether the voxel corresponds to an interior of the organ.

The segmentation neural network described in this specification can be trained using a segmentation loss which includes contributions from only those voxels with the highest error values (e.g., voxels where the segmentation neural network made a confident but incorrect prediction). By using a segmentation loss which includes contributions from only those voxels with the highest error values, the segmentation neural network can be trained to focus on the most difficult and ambiguous parts of medical images. By selecting the contributions to the segmentation loss in this way the training can also take account of the class imbalance which typically arises when imaging organs of disparate sizes, e.g. in a scan of the head the cochlea, 65 mm$^3$ and the brain, 1400000 mm$^3$.

In this manner, the segmentation neural network can be trained to reach an acceptable level of performance over fewer training iterations and training the neural network may therefore consume fewer computational resources (e.g., memory and computing power) than conventional training techniques.

Thus there is also provided a method performed by one or more data processing apparatus for training a segmentation neural network which is configured to process a medical image that is captured using a medical imaging modality and that depicts a region of tissue in a body to generate a segmentation output. The segmentation output may comprise a plurality of segmentation channels, where each segmentation channel corresponds to a respective organ from a predetermined set of organs, and each segmentation channel defines a segmentation of the respective organ corresponding to the segmentation channel in the medical image. A segmentation of a respective organ in the medical image may comprise, for each of a plurality of voxels in the medical image, a respective score characterizing whether the voxel corresponds to an interior of the respective organ. The method may comprise receiving a training medical image; processing the training medical image using the segmentation neural network to generate a training segmentation output; and determining a segmentation loss for the training medical image.

Determining the segmentation loss may comprise, for each segmentation channel of the training segmentation output: determining a set of error values for the segmentation channel, where each error value in the set of error values for the segmentation channel corresponds to a respective voxel in the medical image and is based on an error between: (i) the score from the segmentation channel which characterizes whether the voxel corresponds to the interior of the organ corresponding to the segmentation channel, and (ii) a target score defining whether the voxel corresponds to the interior of the organ corresponding to the segmentation channel; and identifying a plurality of highest error values in the set of error values for the segmentation channel; and determining the segmentation loss based on the plurality of highest error values identified for each segmentation channel of the training segmentation output.

The method may further comprise adjusting current values of segmentation neural network weights based on the segmentation loss for the training medical image.

The error may comprise a cross-entropy loss e.g. a binary cross-entropy loss if the voxel scores are binarized such that the segmentation defines a mask. The method may comprise identifying the plurality of highest error values e.g. highest cross-entropy, in the set of error values for the segmentation channel to be a proper subset of the set of error values for the segmentation channel. Determining the segmentation loss may comprises summing the plurality of highest error values identified. The training may be performed incrementally on image subvolumes e.g. determined by a central image slice and a set of image slices to either side.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification describes a segmentation system that can process a medical image (e.g., a computerized tomography (CT) image) depicting a region of tissue in the body of a patient (e.g., the head and neck region) to generate a segmentation of one or more organs in the region of tissue. More specifically, the segmentation system can generate a segmentation output that specifies, for each voxel of the medical image, whether the voxel is included in each of a predefined set of organs. As used throughout this specification, an "organ" can refer to any appropriate anatomical structure in a body, e.g., the brain, an eye, or a tumor, and certain organs may be partially or wholly contained within other organs, e.g., a lens may be wholly contained within an eye.

Organ segmentations generated by the segmentation system can be used in any of a variety of applications, e.g., in planning radiation therapy (radiotherapy) treatment for patients with cancer. Radiotherapy treatment planning may require accurate segmentation of a target region to be irradiated (e.g., a tumor and areas at high risk of tumor spread) and other organs in the vicinity of the target region, to determine a treatment plan that minimizes the radiation dose received by the other organs. Manual organ segmentation may be time consuming (e.g., an expert can spend four hours or more on a single case) and inconsistent (e.g., between experts, and even within manual segmentations generated by the same expert). In contrast, the segmentation system described in this specification can generate an automatic organ segmentation in seconds or minutes, while (in some cases) achieving a segmentation accuracy that is comparable to that of manual segmentations generated by experts. The segmentation system can thus reduce delays in radiotherapy treatment by partially automating aspects of radiotherapy treatment planning.

These features and other features are described in more detail below.

Figure 1:
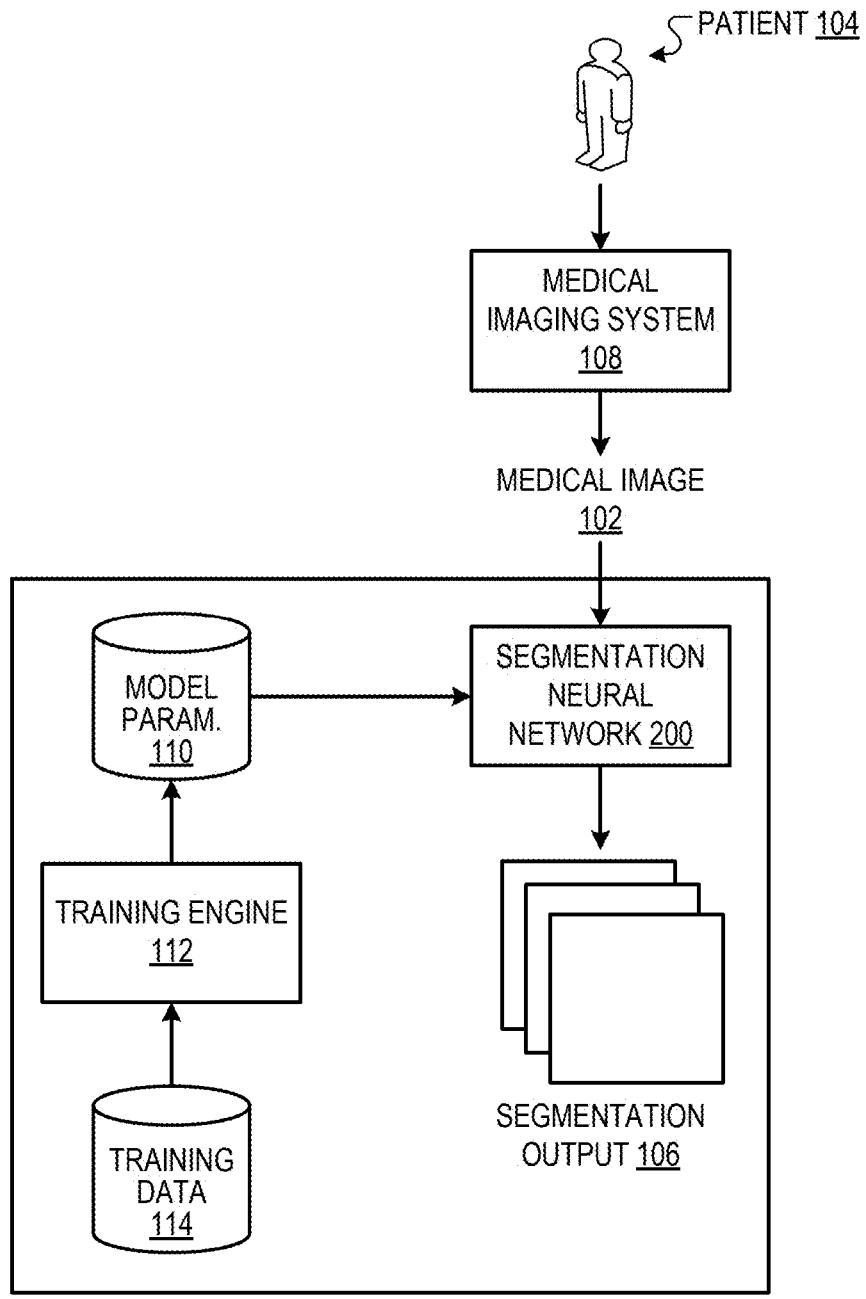
FIG. 1 shows an example segmentation system.

FIG. 1 shows an example segmentation system 100. The segmentation system 100 is an example of a system implemented as computer programs on one or more computers in one or more locations in which the systems, components, and techniques described below are implemented.

The segmentation system 100 is configured to process a medical image 102 that depicts a region of tissue in the body of a patient 104 to generate a segmentation output 106 that defines a segmentation of one or more organs in the medical image 102. An example set of organs in the head and neck region that may be segmented by the segmentation system 100 is described in more detail with reference to FIG. 4.

The medical image 102 may be generated by a medical imaging system 108 using any appropriate medical imaging modality, e.g., computerized tomography (CT), magnetic resonance (MR), or ultrasound (US). In some cases, the segmentation system 100 may be configured to process multiple medical images of the patient, e.g., that are captured using different medical imaging modalities (e.g., a CT image and an MR image), or using the same medical imaging modality (e.g., multiple MR images that are captured in quick succession after a contrast agent is administered to the patient 104). In these cases, the multiple images may be registered prior to being processed by the segmentation system 100. Registering two images refers to applying one or more transformations (e.g., translation, rotation, shearing, or elastic deformation operations) to one of the images to align it with the other image, such that matching voxels in the two images correspond to the same portion of tissue in the patient 104.

The medical image 102 may be represented by a three-dimensional (3-D) array of voxels, where each voxel is associated with an intensity value that characterizes properties of a corresponding portion of tissue in the patient. For example, the intensity values of a CT image characterize the physical density of tissues in the patient, e.g., in Hounsfield units. For convenience, the voxels of the medical image 102 may be referred to in this specification as being indexed by x-, y-, and z-coordinates, and a set of voxels in the medical image 102 having the same value of the z-coordinate may be referred to as a "slice" of the medical image 102.

The segmentation system 100 generates the segmentation output 106 by processing the medical image 102 using a segmentation neural network 200, i.e., in accordance with the values of a set of model parameters 110 of the segmentation neural network 200. Generally, the segmentation neural network 200 is a convolutional neural network, e.g., a 3-D convolutional neural network with one or more 3-D convolutional neural network layers. A 3-D convolutional layer refers to a layer that performs 3-D convolution operations, e.g., using a 3-D convolutional filter, or by performing convolutions using a 2-D convolutional filter in the x-y-dimension followed by a 1-D convolutional filter in the z-dimension. An example architecture of the segmentation neural network is described in more detail with reference to FIG. 2A-D.

The segmentation neural network 200 may be configured to receive an input of a predefined size, e.g., having a predefined number of slices of the medical image 102, e.g., 21 slices. The segmentation output 106 may define a segmentation of only a proper subset of the input, e.g., of only the central slice of the 21 slices of the medical image 102 provided as input, e.g., due to unpadded convolution operations performed in the z-dimension of the input. A convolution operation may be referred to as being padded if the input to the operation is augmented with default values (e.g., zeros), and may otherwise be referred to as being unpadded. Performing an unpadded convolution operation may result in the output of the convolution operation having a lower resolution than the input to the convolution operation. To generate the overall segmentation output 106 for the medical image 102, the segmentation system 100 may process respective subsets of the medical image 102 using the segmentation neural network 200, and then aggregate the respective segmentation outputs 106.

The segmentation output 106 may be represented by an ordered collection of segmentation "channels", where each segmentation channel defines a segmentation of a respective organ in the medical image 102. Each segmentation channel may be represented by an ordered collection of numerical values, e.g., a 3-D array of numerical values, where each numerical value specifies a score characterizing whether a corresponding voxel in the medical image 102 is in the interior of the organ corresponding to the channel. (As used throughout this specification, the "interior" of an organ should be understood to refer to the entirety of the organ, e.g., including the surface of the organ.) A score characterizing whether a voxel is in the interior of an organ may characterize a likelihood that the voxel is in the interior of the organ and may represent, e.g., a probability value between 0 and 1. Optionally, the segmentation system 100 may process the segmentation output 106, e.g., by rounding probability values specified by each channel to corresponding binary values (e.g., 0 or 1) indicating hard predictions for whether corresponding voxels in the medical image 102 are in the interior respective organs.

The segmentation system 100 may use a training engine 112 to train the model parameters 110 of the segmentation neural network 200 on a set of training data 114. The training data 114 may consist of a set of training examples, where each training example specifies: (i) a training medical image, and (ii) a target segmentation that should be generated by the segmentation neural network 200 by processing the training medical image. The target segmentation may be represented by a set of target segmentation channels, i.e., where each target segmentation channel defines the segmentation of a respective organ and may be represented by a 3-D array of numerical values specifying target scores for the voxels of the medical image. The target scores may be binary values, e.g., with the value 1 indicating that a voxel is included in the interior of an organ, and the value 0 indicating otherwise. The target segmentations may be manually generated by an expert, e.g., a radiographer or an oncologist.

The training engine 112 may train the model parameters 110 of the segmentation neural network 200 using an iterative training procedure, e.g., stochastic gradient descent. At each of multiple training iterations, the training engine 112 may select (e.g., sample) a "batch" (set) of training examples from the training data, and process the training medical images specified by the training examples using the segmentation neural network 200 to generate corresponding segmentation outputs 106. The training engine 112 may determine a segmentation loss for each training medical image in the batch that characterizes an error between: (i) the segmentation output generated in accordance with the current values of the model parameters 110 for the training medical image, and (ii) the corresponding target segmentation. The training engine 112 may then determine gradients of the segmentation losses (i.e., with respect to the model parameters 110), and use the gradients to adjust the current values of the model parameters 110 using any appropriate gradient descent optimization algorithm, e.g., RMSprop or Adam.

The training engine 112 may determine the segmentation loss for a training medical image in any of a variety of ways. For example, the training engine 112 may determine the segmentation loss based on the most "difficult" voxels of each segmentation channel, i.e., with the highest errors between the training segmentation channel and the target segmentation channel. More specifically, for each training segmentation channel, the training engine 112 may determine a respective error value between each voxel of the training segmentation channel and the corresponding voxel of the target segmentation channel. The training engine 112 may determine the error value between corresponding voxels of the training segmentation channel and the target segmentation channel in any appropriate manner, e.g., as a cross entropy error. The training engine 112 may then determine the overall segmentation loss as a function (e.g., a sum) of the highest error values from each training segmentation channel (e.g., corresponding to the top 5%, top 10%, or top 15% of error values from each training segmentation channel). Determining the segmentation loss in this manner may speed up training by enabling the segmentation neural network to focus on the most difficult (e.g., ambiguous) voxels of the training medical images.

The training engine 112 may use data augmentation techniques to increase the number of training examples used in training the segmentation neural network. In particular, the training engine 112 may generate new training examples from an existing training example by applying transformation operations to the training medical image specified by the existing training example (and, potentially, to the target segmentation specified by the existing training example). For example, the transformations may include translation, rotation, scaling, shearing, mirroring, elastic deformation, or a combination thereof, that are applied to both the training medical image and the target segmentation, or adding pixel-wise noise to the training medical image (without modifying the target segmentation). Training the segmentation neural network 200 on an augmented set of training data 114 may improve the training the segmentation neural network 200, e.g., by reducing the likelihood of over-fitting and increasing the robustness of the segmentation neural network 200 to variations in its inputs.

The training engine 112 may cease training the model parameters 110 of the segmentation neural network 200 in response to determining that a training termination criterion is satisfied. For example, the training engine 112 may cease training the model parameters 110 in response to determining that a segmentation accuracy of the segmentation neural network 200, evaluated on a set of validation data, has satisfied a predefined threshold. The set of validation data may consist of training examples that are "held-out" from the training of the segmentation neural network 200, i.e., such that the model parameters 110 are not trained on training examples from the validation data.

The training engine 112 may evaluate the segmentation accuracy of the segmentation neural network 200 on the validation data in any of a variety of ways. For example, for each training medical image in the validation data, the training engine 112 may compare the training segmentation (i.e., generated by the segmentation neural network) of each organ of the training medical image to the corresponding target organ segmentation. The training engine 112 may compare two segmentations of an organ by computing a similarity measure between the two segmentations that characterizes a measure of agreement between the surfaces of the two segmentations (e.g., rather than the entire volumes). The measure of agreement between the surfaces of the training segmentation and the target segmentation of an organ may characterize the fraction of the surface of the training segmentation that would need to be manually corrected by an expert, e.g., to enable the segmentation being used in radiotherapy planning.

Figures 3A, 3B:
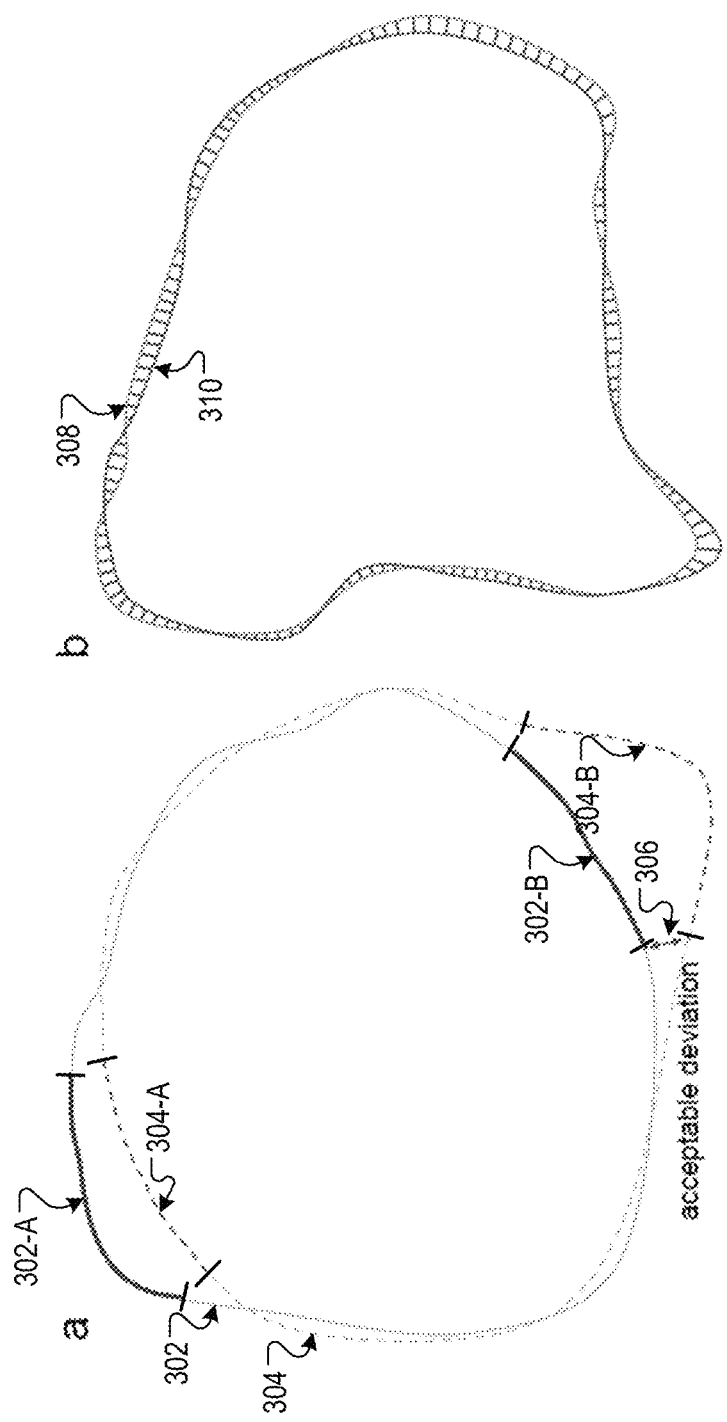
FIG. 3A-3B illustrate an example of computing a surface Dice measure and an organ-specific tolerance threshold.

The training engine 112 may compute the measure of agreement between the surfaces of two segmentations of an organ, e.g., as a "surface Dice measure" that characterizes the fraction of the areas of the two surfaces that are within a tolerance threshold of one another. The tolerance threshold (which can be expressed as a numerical value, e.g., in millimeters), may characterize the maximum acceptable deviation between the surfaces of a training segmentation and a corresponding target segmentation. FIG. 3A provides an illustration of the computation of the surface Dice measure. The tolerance threshold may be an organ-specific value that is computed, e.g., as a percentile (e.g., the 95$^{th}$ percentile, or any other appropriate percentile) of a set of distances between the surfaces of manual segmentations of the organ generated by human experts. A "distance" between the surfaces of two segmentations may refer to the smallest distance between a point on one surface to any point on the other surface. FIG. 3B provides an illustration of a set of distances between the surfaces of two segmentations.

The training engine 112 may compute the surface Dice measure R between two surfaces $S_1$ and $S_2$ at a tolerance threshold $\tau > 0$, e.g., as:

$$R = \frac{|S_1 \cap B_2^\tau| + |S_2 \cap B_1^\tau|}{|S_1| + |S_2|} \quad (1)$$

where $|S_1 \cap B_2^\tau|$ indicates the area of the surface $S_1$ that is in a "tolerance region" $B_2^\tau$ around the surface $S_2$ at the tolerance threshold $\tau$, $|S_2 \cap B_1^\tau|$ indicates the area of the surface $S_2$ that is in a "tolerance region" $B_1^\tau$ around the surface $S_1$ at the tolerance threshold $\tau$, $|S_1|$ indicates the total area of the surface $S_1$, and $|S_2|$ indicates the total area of the surface $S_2$. A tolerance region around a surface S at the tolerance threshold $\tau$ refers to the set of points that are within a distance $\tau$ of the surface, i.e.:

$$B^\tau = \{x \in \mathbb{R}^3 : \exists s \in S, |x-s| \leq \tau\} \quad (2)$$

The training engine 112 may compute the surface areas referenced in equation (1), e.g., by counting the voxels on the respective surfaces. For example, to compute $|S_1 \cap B_2^\tau|$, the training engine 112 may count the number of voxels on the surface $S_1$ that are within a distance $\tau$ of the surface $S_2$. A voxel may be said to be on the surface of a segmentation of an organ, e.g., if it neighbors at least one voxel that is on the exterior of the organ and at least one voxel that is on the interior of the organ. In some implementations, rather than computing the surfaces areas referenced in equation (1) by counting voxels on the surfaces, the training engine 112 may represent each surface as a polygonal mesh (e.g., a triangular mesh, using a marching cube triangulation algorithm), and thereafter compute the surface areas using the mesh. Computing the surface areas using a polygonal mesh may mitigate the possibility of systematic errors that can result from computing the surface areas by voxel counting, e.g., when the voxel spacing is not equal in each spatial dimension.

This approach can also address another problem which is the using "foreground" voxels to represent a surface underestimates the surface area whereas using "background" voxels overestimates the surface area. Thus points defining the polygonal mesh may be placed on a raster that is shifted by one half of the raster spacing on each axis. In 3D each point on this raster has eight neighboring voxels, and the polygon(s) needed to represent each of the $2^8$ possible configurations are defined using the marching cube algorithm, to define surfaces of the segmentation and of the reference segmentation. For each surface area element a distance to the other surface may be calculated, and then the surface area within the tolerance region may be computed by summing the areas of the surfaces elements that are within the tolerance threshold, $\tau$.

The segmentation system 100 may present the segmentation outputs 106 generated by the segmentation neural network 200 to a user of the segmentation system 100, e.g., by generating a visualization that overlays the organ segmentations on the medical image 102. The segmentation system 100 may enable the user to make corrections to the segmentation output 106, e.g., by providing inputs through a user interface. The user may use the segmentation output as part of planning radiotherapy treatment for the patient 104.

Figure 2A:
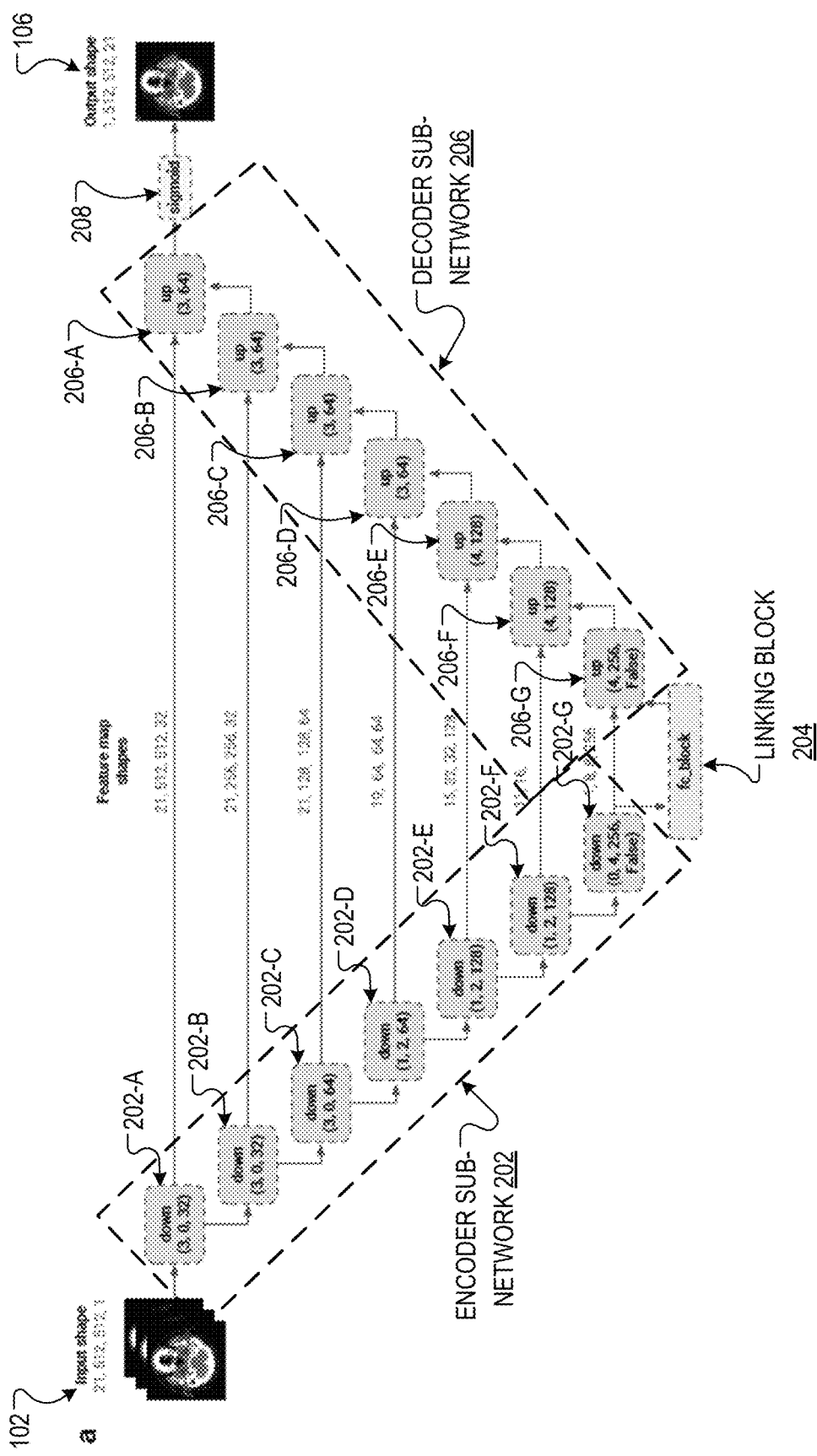
FIG. 2A-2D illustrate an example architecture of a segmentation neural network.

FIG. 2A illustrates an example architecture of the segmentation neural network 200. In this example, the segmentation neural network 200 has an encoder sub-network 202, a linking block 204, and a decoder sub-network 206. As used throughout this specification, a "block" refers to a group of one or more neural network layers. Generally, the input and the output of a block may be represented as an array of numerical values that are indexed along multiple "spatial" dimensions (e.g., x-y dimensions, or z-x-y dimensions) and a "channel" dimension. The "resolution" of a block input/output along a dimension refers to the number of index values along that dimension. A block may be referred to as a "residual" block if an intermediate output of a first layer of the block (or the input to the block) is added to the intermediate output of a subsequent layer of the block (or to the output of the block).

The encoder sub-network 202 includes a sequence of multiple encoder blocks, e.g., the encoder blocks 202-A-G, each of which include 2-D convolutional layers, 3-D convolutional layers, or both. Each encoder block is configured to process an encoder block input to generate an encoder block output having a lower spatial resolution than the encoder block input, i.e., such that the resolution of the encoder block output is less than the resolution of the encoder block input along at least one spatial dimension. The first encoder block 202-A may be configured to process the medical image 102, while each subsequent encoder block 202-B-G may be configured to process the encoder block output of the preceding encoder block in the encoder sub-network 202. An example encoder block architecture is illustrated with reference to FIG. 2B.

The linking block 204 is configured to process a linking block input that includes the output of the final encoder block 202-G in the encoder sub-network 202 to generate a linking block output that is provided as an input to the decoder sub-network 206. An example linking block architecture is illustrated with reference to FIG. 2C.

The decoder sub-network 206 includes a sequence of multiple decoder blocks, e.g., the decoder blocks 206-A-G, each of which include 2-D convolutional layers, 3-D convolutional layers, or both. Each decoder block is configured to process a decoder block input to generate a decoder block output having a higher spatial resolution than the decoder block input, i.e., such that the resolution of the decoder block output is higher than the resolution of the decoder block input along at least one spatial dimension. The first decoder block 206-G may be configured to process an input including: (i) the linking block output, and (ii) an intermediate output of a corresponding encoder block 202-G. Each subsequent decoder block 206-A-F may be configured to process: (i) an intermediate output of a corresponding encoder block, and (ii) the decoder block output of the preceding decoder block in the decoder sub-network. For example, the decoder block 206-F may be configured to process: (i) the intermediate output of the corresponding encoder block 202-F, and (ii) the output of the decoder block 206-G. In this specification, an "intermediate output" of an encoder block refers to an output generated by any layer of the encoder block excluding the input layer of the encoder block. An example decoder block architecture is illustrated with reference to FIG. 2D.

The segmentation neural network 200 is configured to process the output of the final decoder block 206-A using an output layer 208 ("final layer") to generate the segmentation output 106. The output layer 208 optionally processes the output of the final decoder block 206-A in accordance with a set of output layer weights (e.g., defining one or more convolution operations), and then applies a non-linear "activation" function (e.g., a sigmoid activation function) separately to each component of the segmentation output 106. By applying the activation function separately to each component of the segmentation output 106, the segmentation neural network can characterize a single voxel of the medical image 102 as being likely to belong to multiple organs. That is, the segmentation neural network can generate a segmentation output that assigns a "high" probability (e.g., a probability close to 1) to matching components of different segmentation channels, i.e., components that correspond to the same voxel in the medical image 102. For example, the segmentation neural network can generate a segmentation output which characterizes a single voxel as being highly likely to belong to both a "spinal cord" and a "spinal canal".

Applying an activation jointly to groups of the components of the segmentation output 106 (i.e., rather than separately to each component of the segmentation output 106) may result in the segmentation output being unable to characterize a single voxel as belonging to multiple overlapping organs. For example, a soft-max activation function may be jointly applied to groups of components of the segmentation output, where all the components in a group correspond to the same voxel in the medical image, and the soft-max outputs for the components of each group sum to 1. Requiring the probabilities that a given voxel belongs to each organ to sum to 1 results in the segmentation output 106 being unable to characterize a single voxel as being highly likely to belong to multiple organs.

Figure 2B:
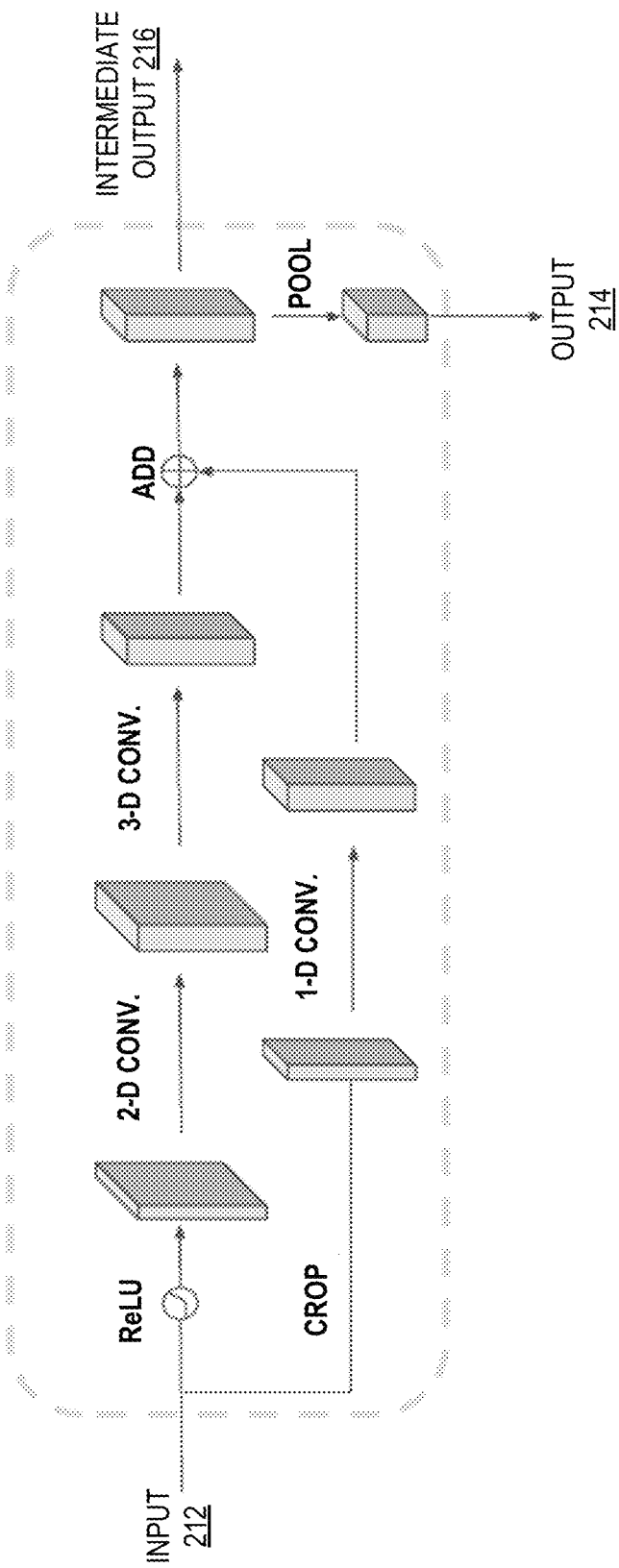

FIG. 2B illustrates an example architecture of an encoder block 210 of the encoder sub-network of the segmentation neural network. The encoder block 210 is configured to process a block input 212 to generate a block output 214 (having a lower spatial resolution than the block input 212) and an intermediate output 216, as described above. In the illustration, "ReLU" refers to a rectified linear unit activation function, "1-D Cony" refers to 1-D convolution operations, "2-D Cony" refers to 2-D convolution operations, "3-D Cony" refers to 3-D convolution operations, "Pool" refers to pooling operations, "Crop" refers to cropping the block input centrally in the z-dimension, and "Add" refers to an addition operation. Various illustrated features of the example architecture of the encoder block 210 are optional; for example, the encoder block 210 may exclude the 2-D, the 3-D convolution operations, or the pooling operation (or a combination thereof). In one example, the 2-D convolution operations may be implemented by repeatedly applying 1×3×3-dimensional (in z-x-y coordinates) convolution kernels followed by a ReLU, the 3-D convolution operations may be implemented by repeatedly applying 1×3×3-dimensional convolution kernels followed by 3×1×1-dimensional convolution kernels and a ReLU, and the pooling operation may be implemented as a 1×2×2-dimensional average pooling operation.

Figure 2C:
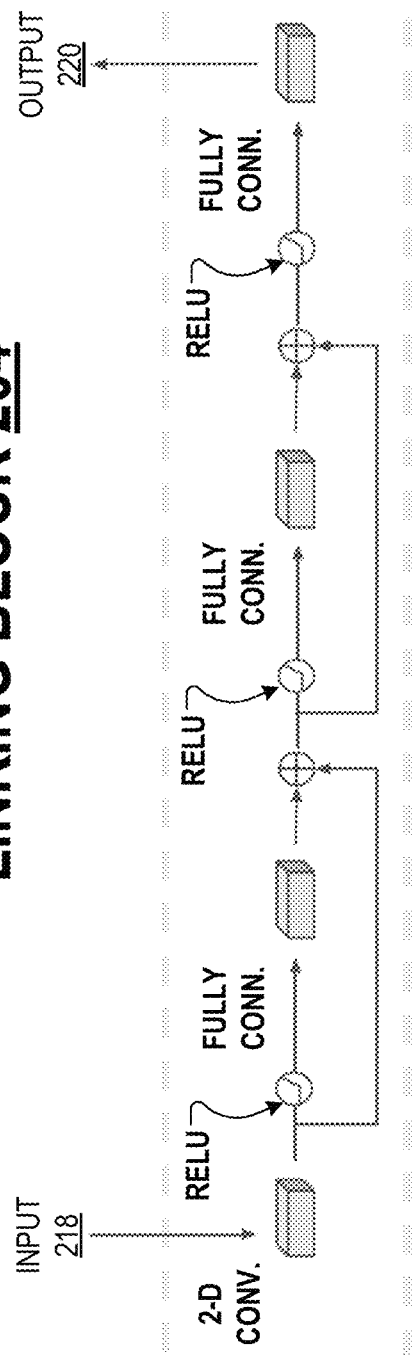

FIG. 2C illustrates an example architecture of a linking block 204 of the segmentation neural network. The linking block 204 is configured to process a block input 218 (generated by the final encoder block) to generate a block output 220 (which is provided to the first decoder block). In the illustration, "Fully Conn" refers to the operations performed by a fully-connected neural network layer, and "2-D Cony" and "ReLU" are defined with reference to FIG. 2B. In one example, the 2-D convolution operations may be implemented by applying 1×8×8-dimensional convolution kernels.

Figure 2D:
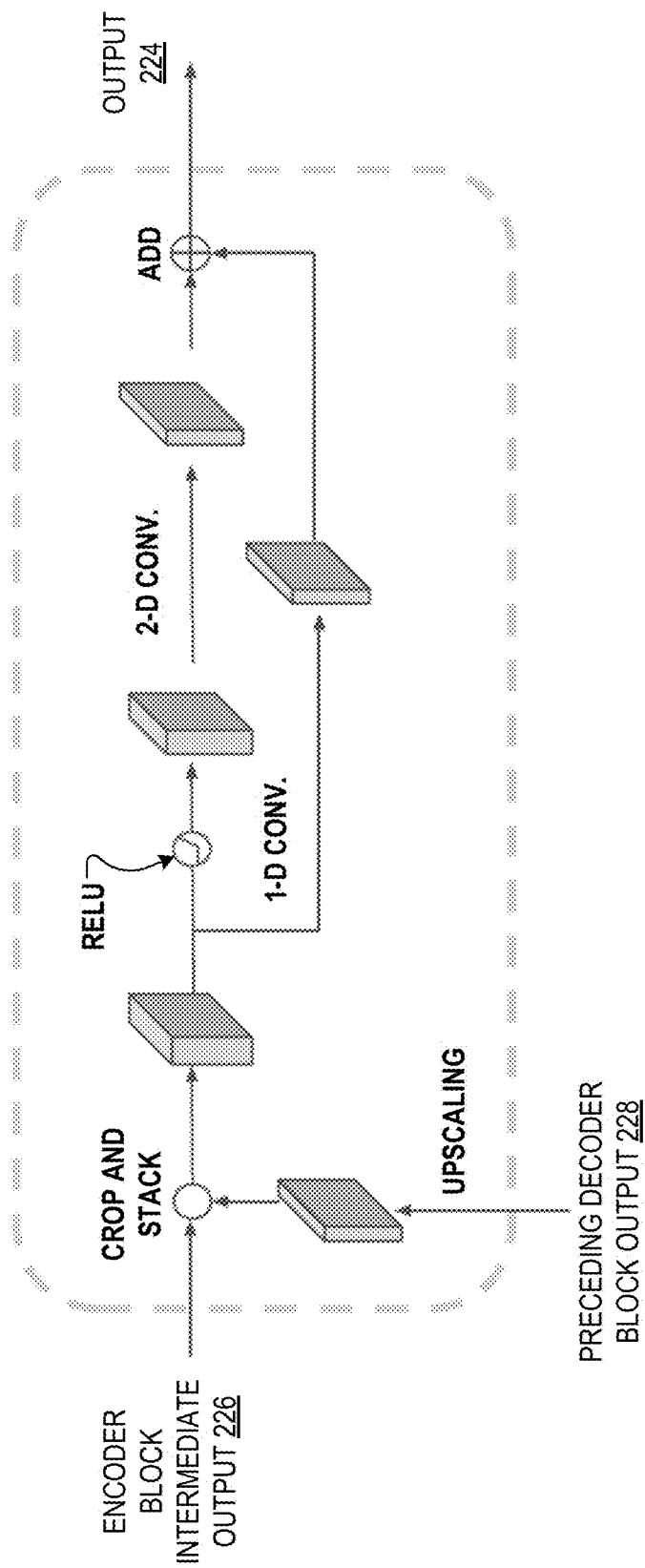

FIG. 2D illustrates an example architecture of a decoder block 222 of the decoder sub-network of the segmentation neural network. The decoder block 222 is configured to process a decoder block input to generate a decoder block output 224 having a higher spatial resolution than the block input, as described above. Generally, the decoder block input includes: (i) an intermediate output 226 of a corresponding encoder block, and (ii) the output of the preceding decoder block 228 or the output of the linking block. For convenience, FIG. 2D illustrates the decoder block 222 as receiving the preceding decoder block output 228 rather than the linking block output. In the illustration, "Upscaling" refers to an operation that operates on an input to increase the spatial resolution of the input, "Crop and Stack" refers to cropping the encoder block intermediate output 226 in the z-dimension and concatenating the result with the upscaled preceding decoder block output 228, and "ReLU", "1-D Cony", "2-D Cony", and "Add" are defined with reference to FIG. 2B. In one example, the 2-D convolution operations may be implemented by applying 1×3×3-dimensional convolution kernels.

FIG. 3A illustrates an example of the computation of the surface Dice measure. For convenience, FIG. 3A illustrates an example of computing the surface Dice measure in 2-D, but more generally, the surface Dice measure may be computed in 3-D to characterize a measure of agreement between 3-D organ segmentations. In this example, the continuous line 302 represents the surface of a predicted organ segmentation generated using the segmentation neural network (described with reference to FIG. 1), and the dashed line 304 represents the surface of a target organ segmentation (e.g., generated manually by a radiographer). The arrow 306 represents the tolerance threshold, i.e., the maximum acceptable margin of deviation. The darkened line segments 302-A, 302-B, 304-A, and 304-B represent the portions of the surfaces where the distance between them exceeds the tolerance threshold. The surface Dice measure characterizes the areas of the surfaces that are within the tolerance threshold of one another compared to the total surface areas, as described with reference to FIG. 1.

FIG. 3B illustrates the determination of an organ-specific tolerance threshold. For convenience, FIG. 3B (as with FIG. 3A) illustrates segmentations in 2-D, but more generally, the segmentations of organs may be in 3-D. The lines 308 and 310 represent the surfaces of two segmentations of an organ that were manually generated by different experts, and the line segments between the lines 308 and 310 represent distances between the two surfaces. The organ-specific tolerance may be defined, e.g., as the $95^{th}$ percentile of the distances between surfaces of manual segmentations of the organ.

Figure 4:
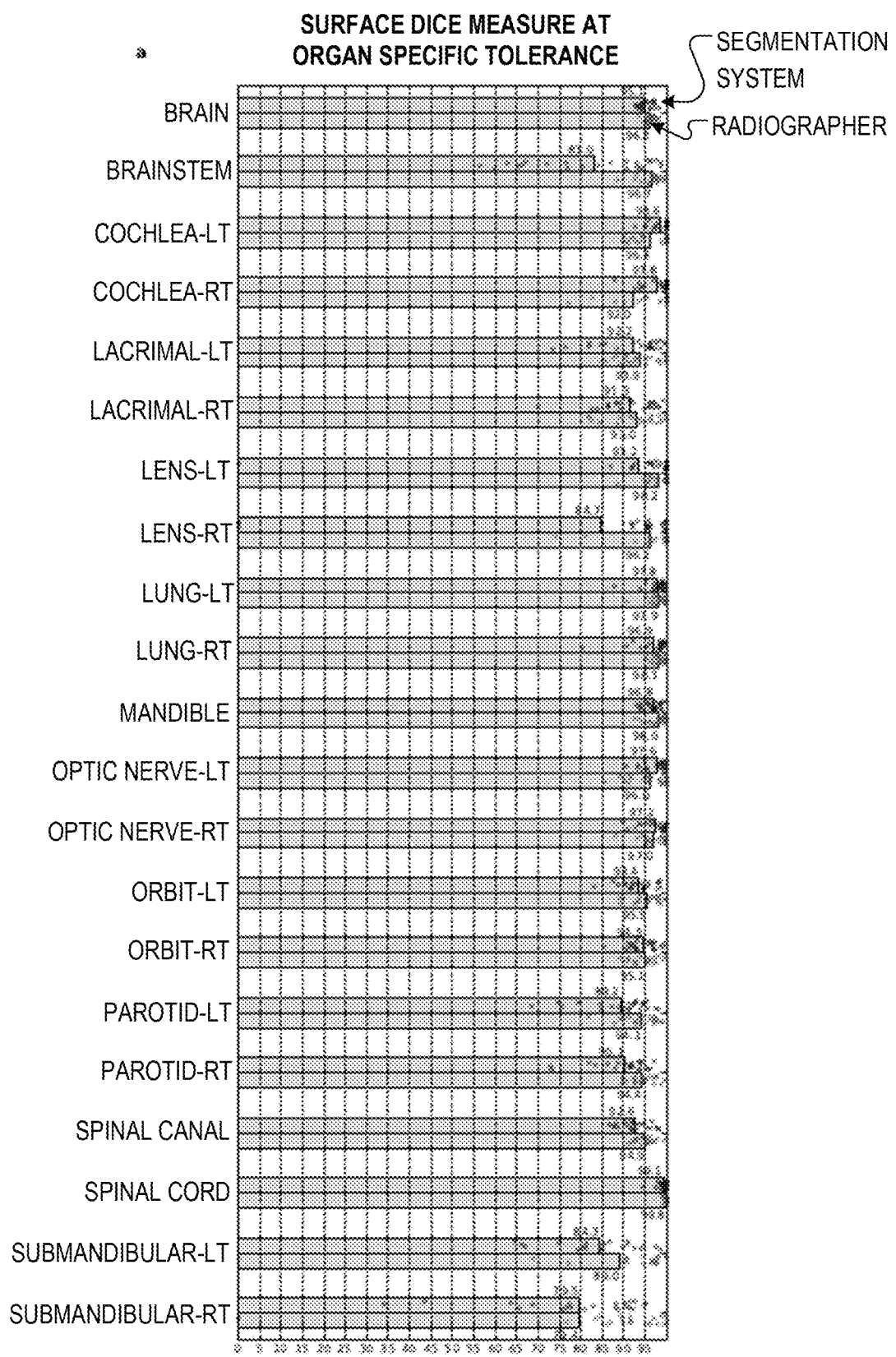
FIG. 4 illustrates an example of the quantitative performance of the segmentation system in comparison to radiographers.

FIG. 4 illustrates an example of the quantitative performance of the segmentation system in comparison to radiographers. For each of multiple organs (e.g., brain, brainstem, cochlea-lt, etc.), the first bar shows the mean value of the surface Dice measure for organ segmentations generated by the segmentation system compared to gold standard segmentations, and the second bar shows the mean value of the surface Dice measure for organ segmentations generated by radiographers compared to gold standard segmentations. For 19 out of 21 organs, there was no substantial difference between the performance of the segmentation system and the performance of the radiographers (where a substantial difference is defined as 5% or more).

Figure 5:
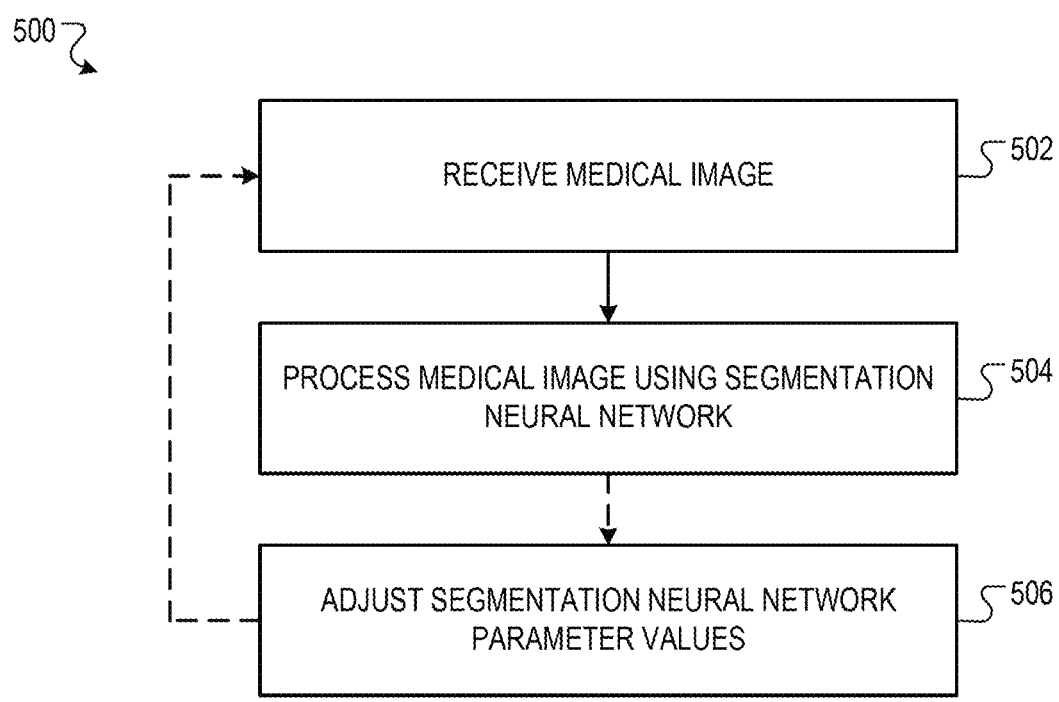
FIG. 5 is a flow diagram of an example process for training and using a segmentation neural network.

FIG. 5 is a flow diagram of an example process 500 for training and using a segmentation neural network. For convenience, the process 500 will be described as being performed by a system of one or more computers located in one or more locations. For example, a segmentation system, e.g., the segmentation system 100 of FIG. 1, appropriately programmed in accordance with this specification, can perform the process 500.

The system receives a medical image that is captured using a medical imaging modality and that depicts a region of tissue in a body (502). The medical imaging modality may be, e.g., a computerized tomography (CT) modality. The region of tissue in the body may be, e.g., a head and neck region.

The system processes the medical image using a segmentation neural network to generate a segmentation output (504). The segmentation output may include a set of segmentation channels, where each segmentation channel corresponds to a respective organ from a predetermined set of organs and defines a segmentation of the organ in the medical image. A segmentation of an organ in the medical image specifies, for each of multiple voxels in the medical image, a score characterizing whether the voxel corresponds to the interior of the organ. The predetermined set of organs may include one or more organs at risk in a patient receiving radiotherapy treatment. The segmentation output may be used in radiotherapy treatment planning.

The segmentation neural network may include an encoder subnetwork with a sequence of multiple encoder blocks, where each encoder block is a residual neural network block including one or more two-dimensional convolutional neural network layers, one or more three-dimensional convolutional neural network layers, or both. Each encoder block may be configured to process an encoder block input to generate an encoder block output having a lower spatial resolution than the encoder block input. Each encoder block after the first encoder block may process an input that includes the output of the previous encoder block. The three-dimensional convolutional neural network layers in the encoder blocks may include padded xy-convolutions and unpadded z-convolutions.

The segmentation neural network may include a linking block that includes a fully-connected neural network layer. The linking block may be configured to process a linking block input that includes the output of the final encoder block to generate a linking block output.

The segmentation neural network may include a decoder subnetwork with a sequence of multiple decoder blocks, where each decoder block is a residual neural network block that includes one or more two-dimensional convolutional neural network layers, one or more three-dimensional convolutional neural network layers, or both. Each decoder block is configured to process a decoder block input to generate a decoder block output having a spatial resolution that is higher than the decoder block input. The first decoder block may be configured to process an input that includes the linking block output, and each subsequent decoder block may be configured to process an input that includes: (i) an intermediate output of a respective encoder block, and (ii) the output of the previous decoder block.

The segmentation neural network may include a final layer that is configured to process a final layer input (e.g., from the decoder sub-network) to generate the segmentation output. The final layer may process the final layer input in accordance with the values of a set of final layer weights to generate a transformed final layer input, and then process the transformed final layer input using a sigmoid activation function to generate the segmentation output.

The system may compute a surface Dice measure between: (i) a segmentation of an organ in the medical image defined by a segmentation channel of the segmentation output, and (ii) a reference (target) segmentation of the organ in the medical image. For example, the system may determine a first number of voxels in the intersection of: (i) the surface of the segmentation, and (ii) a tolerance region around the surface of the reference segmentation. The system may determine a second number of voxels in the intersection of: (i) the surface of the reference segmentation, and (ii) a tolerance region around the surface of the segmentation. The system may determine the surface Dice measure as a ratio of: (i) the sum of the first number of voxels and the second number of voxels, and (ii) the sum of the number of voxels in the surfaces of the segmentation and the target segmentation.

During training, the system adjusts the current values of the segmentation neural network weights (506). In particular, the system determines a segmentation loss for the medical image by determining a respective set of error values for each channel of the segmentation output. Each error value in the set of error values for a segmentation channel corresponds to a respective voxel in the medical image and is based on an error between: (i) the score from the segmentation channel which characterizes whether the voxel corresponds to the interior of the organ corresponding to the segmentation channel, and (ii) a target score defining whether the voxel corresponds to the interior of the organ corresponding to the segmentation channel. The system may compute the error, e.g., as a cross-entropy error. The system identifies a respective set of highest error values for each segmentation channel (e.g., as a "proper subset" of the total set of error values for the segmentation channel), and determines the segmentation loss based on the highest error values for each segmentation channel. For example, the system may determine the segmentation loss by summing the highest error values for each segmentation channel. The system then adjusts the current values of the segmentation neural network weights based on the segmentation loss, e.g., by backpropagating gradients of the segmentation loss through the segmentation neural network weights.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method performed by one or more data processing apparatus, the method comprising:
   receiving a medical image that is captured using a medical imaging modality and that depicts a region of tissue in a body;
   processing the medical image using a segmentation neural network, in accordance with trained values of a plurality segmentation neural network parameters, to generate a segmentation output, wherein:
      the segmentation output comprises a plurality of segmentation channels, each segmentation channel corresponds to a respective organ from a predetermined set of organs, and each segmentation channel defines a segmentation of the respective organ corresponding to the segmentation channel in the medical image;
      a segmentation of a respective organ in the medical image comprises, for each of a plurality of voxels in the medical image, a respective score characterizing whether the voxel corresponds to an interior of the respective organ;
      the segmentation neural network comprises a sequence of multiple encoder blocks, wherein:
         each encoder block is a residual neural network block comprising one or more two-dimensional convolutional neural network layers, one or more three-dimensional convolutional neural network layers, or both;
         each encoder block is configured to process a respective encoder block input to generate a respective encoder block output wherein a spatial resolution of the encoder block output is lower than a spatial resolution of the encoder block input; and
         for each encoder block that is after an initial encoder block in the sequence of encoder blocks, the encoder block input comprises a previous encoder block output of a previous encoder block in the sequence of encoder blocks;
      the segmentation neural network comprises a decoder subnetwork, wherein the decoder subnetwork is configured to process a decoder subnetwork input comprising an intermediate output of each encoder block to generate the segmentation output;
      the decoder subnetwork comprises a final layer that is configured to process a final layer input to generate the segmentation output;
   wherein the segmentation neural network has been trained by a plurality of operations comprising:
   processing a training medical image using the segmentation neural network to generate a training segmentation output;
   determining a segmentation loss for the training medical image, comprising:

for each segmentation channel of the training segmentation output:
  determining a set of error values for the segmentation channel, wherein each error value in the set of error values for the segmentation channel corresponds to a respective voxel in the training medical image and is based on an error between: (i) the score from the segmentation channel which characterizes whether the voxel corresponds to the interior of the organ corresponding to the segmentation channel, and (ii) a target score defining whether the voxel corresponds to the interior of the organ corresponding to the segmentation channel; and
  identifying a plurality of highest error values from the set of error values for the segmentation channel, wherein the plurality of highest error values are a proper subset of the set of error values for the segmentation channel; and
  determining the segmentation loss based on the plurality of highest error values identified for each segmentation channel of the training segmentation output; and
adjusting current values of the plurality of segmentation neural network parameters of the segmentation neural network based on the segmentation loss for the training medical image.

2. The method of claim 1, wherein processing the final layer input to generate the segmentation output comprises:
  processing the final layer input in accordance with a set of final layer parameters to generate a transformed final layer input; and
  applying a non-linear activation function to each component of the transformed final layer input to generate the segmentation output, wherein the non-linear activation function is configured to process an input consisting of a single scalar value to generate an output consisting of a single scalar value.

3. The method of claim 2, wherein the non-linear activation function is a sigmoid activation function.

4. The method of claim 1, wherein for one or more voxels of the medical image, the segmentation output defines that the voxel is included in each of multiple overlapping organs.

5. The method of claim 1, wherein the medical imaging modality is a computerized tomography (CT) medical imaging modality.

6. The method of claim 1, wherein the region of tissue in the body that is depicted by the medical image comprises a head and neck region.

7. The method of claim 1, wherein the predetermined set of organs comprise one or more organs at risk in a patient receiving radiotherapy treatment.

8. The method of claim 1, further comprising using the segmentation output in radiotherapy treatment planning.

9. The method of claim 1, wherein the decoder subnetwork comprises a sequence of multiple decoder blocks, wherein:
  each decoder block is a residual neural network block comprising one or more two-dimensional convolutional neural network layers;
  each decoder block is configured to process a respective decoder block input to generate a respective decoder block output, wherein a spatial resolution of the decoder block output is greater than a resolution of the decoder block input; and
  for each decoder block that is after an initial decoder block in the sequence of decoder blocks, the decoder block input comprises: (i) an intermediate output of a respective encoder block, and (ii) a previous decoder block output of a previous decoder block.

10. The method of claim 1, wherein the three-dimensional convolutional neural network layers in the encoder blocks comprise padded xy-convolutions and unpadded z-convolutions.

11. The method of claim 1, wherein the segmentation neural network comprises a linking block, wherein:
  the linking block is a residual neural network block comprising a fully-connected layer;
  the linking block is configured to process a linking block input comprising an output of a final encoder block in the sequence of encoder blocks to generate a linking block output; and
  the linking block output is provided as an input to the decoder subnetwork.

12. The method of claim 1, further comprising computing a surface Dice measure between: (i) a segmentation of a respective organ in the medical image defined by a segmentation channel from the segmentation output, and (ii) a reference segmentation of the respective organ in the medical image, comprising:
  determining a number of voxels in a first intersection between: (i) a surface of the segmentation of the respective organ, and (ii) a tolerance region around a surface of the reference segmentation of the respective organ;
  determining a number of voxels in a second intersection between: (i) a surface of the reference segmentation of the respective organ, and (ii) a tolerance region around a surface of the segmentation of the respective organ; and
  determining the surface dice measure as a ratio of: (i) a sum of the number of voxels in the first intersection and the number of voxels in the second intersection, and (ii) a sum of a number of voxels in the surface of the segmentation of the respective organ and a number of voxels in the surface of the reference segmentation of the respective organ.

13. A system comprising:
one or more computers; and
one or more storage devices communicatively coupled to the one or more computers, wherein the one or more storage devices store instructions that, when executed by the one or more computers, cause the one or more computers to perform operations comprising:
receiving a medical image that is captured using a medical imaging modality and that depicts a region of tissue in a body;
processing the medical image using a segmentation neural network, in accordance with trained values of a plurality segmentation neural network parameters, to generate a segmentation output, wherein:
  the segmentation output comprises a plurality of segmentation channels, each segmentation channel corresponds to a respective organ from a predetermined set of organs, and each segmentation channel defines a segmentation of the respective organ corresponding to the segmentation channel in the medical image;
  a segmentation of a respective organ in the medical image comprises, for each of a plurality of voxels in the medical image, a respective score characterizing whether the voxel corresponds to an interior of the respective organ;

the segmentation neural network comprises a sequence of multiple encoder blocks, wherein:
  each encoder block is a residual neural network block comprising one or more two-dimensional convolutional neural network layers, one or more three-dimensional convolutional neural network layers, or both;
  each encoder block is configured to process a respective encoder block input to generate a respective encoder block output wherein a spatial resolution of the encoder block output is lower than a spatial resolution of the encoder block input; and
  for each encoder block that is after an initial encoder block in the sequence of encoder blocks, the encoder block input comprises a previous encoder block output of a previous encoder block in the sequence of encoder blocks;
the segmentation neural network comprises a decoder subnetwork, wherein the decoder subnetwork is configured to process a decoder subnetwork input comprising an intermediate output of each encoder block to generate the segmentation output;
the decoder subnetwork comprises a final layer that is configured to process a final layer input to generate the segmentation output;
wherein the segmentation neural network has been trained by a plurality of operations comprising:
processing a training medical image using the segmentation neural network to generate a training segmentation output;
determining a segmentation loss for the training medical image, comprising:
  for each segmentation channel of the training segmentation output:
    determining a set of error values for the segmentation channel, wherein each error value in the set of error values for the segmentation channel corresponds to a respective voxel in the training medical image and is based on an error between: (i) the score from the segmentation channel which characterizes whether the voxel corresponds to the interior of the organ corresponding to the segmentation channel, and (ii) a target score defining whether the voxel corresponds to the interior of the organ corresponding to the segmentation channel; and
    identifying a plurality of highest error values from the set of error values for the segmentation channel, wherein the plurality of highest error values are a proper subset of the set of error values for the segmentation channel; and
  determining the segmentation loss based on the plurality of highest error values identified for each segmentation channel of the training segmentation output; and
adjusting current values of the plurality of segmentation neural network parameters of the segmentation neural network based on the segmentation loss for the training medical image.

14. The system of claim 13, wherein processing the final layer input to generate the segmentation output comprises:
  processing the final layer input in accordance with a set of final layer parameters to generate a transformed final layer input; and
  applying a non-linear activation function to each component of the transformed final layer input to generate the segmentation output, wherein the non-linear activation function is configured to process an input consisting of a single scalar value to generate an output consisting of a single scalar value.

15. The system of claim 14, wherein the non-linear activation function is a sigmoid activation function.

16. The system of claim 13, wherein for one or more voxels of the medical image, the segmentation output defines that the voxel is included in each of multiple overlapping organs.

17. One or more non-transitory computer storage media storing instructions that when executed by one or more computers cause the one or more computers to perform operations comprising:
receiving a medical image that is captured using a medical imaging modality and that depicts a region of tissue in a body;
processing the medical image using a segmentation neural network, in accordance with trained values of a plurality segmentation neural network parameters, to generate a segmentation output, wherein:
  the segmentation output comprises a plurality of segmentation channels, each segmentation channel corresponds to a respective organ from a predetermined set of organs, and each segmentation channel defines a segmentation of the respective organ corresponding to the segmentation channel in the medical image;
  a segmentation of a respective organ in the medical image comprises, for each of a plurality of voxels in the medical image, a respective score characterizing whether the voxel corresponds to an interior of the respective organ;
  the segmentation neural network comprises a sequence of multiple encoder blocks, wherein:
    each encoder block is a residual neural network block comprising one or more two-dimensional convolutional neural network layers, one or more three-dimensional convolutional neural network layers, or both;
    each encoder block is configured to process a respective encoder block input to generate a respective encoder block output wherein a spatial resolution of the encoder block output is lower than a spatial resolution of the encoder block input; and
    for each encoder block that is after an initial encoder block in the sequence of encoder blocks, the encoder block input comprises a previous encoder block output of a previous encoder block in the sequence of encoder blocks;
  the segmentation neural network comprises a decoder subnetwork, wherein the decoder subnetwork is configured to process a decoder subnetwork input comprising an intermediate output of each encoder block to generate the segmentation output;
  the decoder subnetwork comprises a final layer that is configured to process a final layer input to generate the segmentation output;
wherein the segmentation neural network has been trained by a plurality of operations comprising:
processing a training medical image using the segmentation neural network to generate a training segmentation output;
determining a segmentation loss for the training medical image, comprising:
  for each segmentation channel of the training segmentation output:
    determining a set of error values for the segmentation channel, wherein each error value in the set of error values for the segmentation channel corresponds to a respective voxel in the training medical image and is based on an error between: (i) the score from the segmentation channel which characterizes whether the voxel corresponds to the interior of the organ corresponding to the segmentation channel, and (ii) a target score defining whether the voxel corresponds to the interior of the organ corresponding to the segmentation channel; and identifying a plurality of highest error values from the set of error values for the segmentation channel, wherein the plurality of highest error values are a proper subset of the set of error values for the segmentation channel; and determining the segmentation loss based on the plurality of highest error values identified for each segmentation channel of the training segmentation output; and adjusting current values of the plurality of segmentation neural network parameters of the segmentation neural network based on the segmentation loss for the training medical image.

18. The non-transitory computer storage media of claim 17, wherein processing the final layer input to generate the segmentation output comprises:

processing the final layer input in accordance with a set of final layer parameters to generate a transformed final layer input; and applying a non-linear activation function to each component of the transformed final layer input to generate the segmentation output, wherein the non-linear activation function is configured to process an input consisting of a single scalar value to generate an output consisting of a single scalar value.

19. The non-transitory computer storage media of claim 18, wherein the non-linear activation function is a sigmoid activation function.

20. The non-transitory computer storage media of claim 17, wherein for one or more voxels of the medical image, the segmentation output defines that the voxel is included in each of multiple overlapping organs.

* * * * *